(12) United States Patent
Liu

(10) Patent No.: US 9,894,932 B2
(45) Date of Patent: Feb. 20, 2018

(54) BATTERY ASSEMBLY, ATOMIZING ASSEMBLY OF ELECTRONIC CIGARETTE AND ELECTRONIC CIGARETTE

(71) Applicant: KIMREE HI-TECH INC., Tortola (VG)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 0 days.

(21) Appl. No.: 14/366,045

(22) PCT Filed: Dec. 30, 2013

(86) PCT No.: PCT/CN2013/090902
§ 371 (c)(1),
(2) Date: Jun. 17, 2014

(87) PCT Pub. No.: WO2015/078085
PCT Pub. Date: Jun. 4, 2015

(65) Prior Publication Data
US 2016/0262451 A1   Sep. 15, 2016

(30) Foreign Application Priority Data

Nov. 29, 2013   (CN) .................... 2013 2 0778454 U

(51) Int. Cl.
*A24F 47/00*   (2006.01)
*H02J 7/00*   (2006.01)
(Continued)

(52) U.S. Cl.
CPC .......... *A24F 47/008* (2013.01); *G01N 21/84* (2013.01); *H05B 1/02* (2013.01); *H05B 1/0244* (2013.01); *H05B 1/0297* (2013.01)

(58) Field of Classification Search
None
See application file for complete search history.

(56) References Cited

U.S. PATENT DOCUMENTS 5,967,148 A * 10/1999 Harris ................... A24F 47/008
                                                       131/329
2013/0220315 A1* 8/2013 Conley ................. A24F 47/008
                                                       128/202.21
(Continued)

FOREIGN PATENT DOCUMENTS

| CN | 101189613 A  | 5/2008  |
| CN | 202996169 U  | 6/2013  |
| CN | 203219932 U  | 10/2013 |

OTHER PUBLICATIONS

International Search Report: International Application No. PCT/CN2013/090902; International filing date Aug. 8, 2014, no English translation available.

*Primary Examiner* — Joseph M Pelham
(74) *Attorney, Agent, or Firm* — U.S. Fairsky LLP; Yue (Robert) Xu

(57) ABSTRACT

A battery assembly of an electronic cigarette according to the present application is adapted to form an electronic cigarette in combination with an atomizing assembly. The atomizer of the electronic cigarette is provided with a substance to be detected, and the battery assembly is provided with a spectrum identification device and a microcontroller. The spectrum identification device is arranged on the battery assembly and is configured to obtain spectrum information of the substance to be detected. The microcontroller is connected with the spectrum identification device and configured to determine whether the spectrum information of the substance to be detected matches a preset information, and in a case that the spectrum information of the substance to be detected matches the preset information,
(Continued)

the microcontroller controls a circuit between the battery assembly and the atomizing assembly to be switched on to enable the electronic cigarette to work normally.

20 Claims, 9 Drawing Sheets

(51) Int. Cl.
  *G01N 21/84* (2006.01)
  *H05B 1/02* (2006.01)

(56) References Cited

U.S. PATENT DOCUMENTS

| | | | | |
|---|---|---|---|---|
| 2014/0299138 | A1* | 10/2014 | Xiang | A24F 47/008 131/329 |
| 2015/0075545 | A1* | 3/2015 | Xiang | A24F 47/008 131/329 |
| 2015/0101625 | A1* | 4/2015 | Newton | H05B 1/0244 131/329 |
| 2015/0189695 | A1* | 7/2015 | Xiang | G06K 7/10861 219/209 |
| 2015/0208731 | A1* | 7/2015 | Malamud | H05B 1/0244 131/328 |
| 2015/0224268 | A1* | 8/2015 | Henry | A24F 47/008 128/202.21 |
| 2015/0258289 | A1* | 9/2015 | Henry, Jr. | A61M 15/06 128/202.21 |
| 2016/0029698 | A1* | 2/2016 | Xiang | H04B 5/0025 131/328 |
| 2016/0278431 | A1* | 9/2016 | Liu | G06K 9/325 |
| 2016/0345627 | A1* | 12/2016 | Liu | A24F 47/008 |
| 2016/0374392 | A1* | 12/2016 | Liu | H02J 7/0052 392/404 |
| 2016/0374402 | A1* | 12/2016 | Fernando | A24F 47/008 392/404 |
| 2017/0013882 | A1* | 1/2017 | Liu | A24F 47/008 |
| 2017/0020191 | A1* | 1/2017 | Lamb | A24F 47/008 |
| 2017/0135408 | A1* | 5/2017 | Cameron | A24F 47/008 |

* cited by examiner

BATTERY ASSEMBLY, ATOMIZING ASSEMBLY OF ELECTRONIC CIGARETTE AND ELECTRONIC CIGARETTE

This application is the U.S. national stage of International Application No. PCT/CN2013/090902, titles "BATTERY ASSEMBLY, ATOMIZING ASSEMBLY OF ELECTRONIC CIGARETTE AND ELECTRONIC CIGARETTE", filed on Dec. 30, 2013, which claims the benefit of priority to Chinese patent application No. 201320778454.2, titled "BATTERY ASSEMBLY, ATOMIZING ASSEMBLY OF ELECTRONIC CIGARETTE AND ELECTRONIC CIGARETTE" and filed with the Chinese State Intellectual Property Office on Nov. 29, 2013, both of which application are incorporated herein in their entireties by this reference.

FIELD

The present application relates to the technical filed of electronic cigarettes, and in particular to a battery assembly and an atomizing assembly of an electronic cigarette and an electronic cigarette.

BACKGROUND

An existing electronic cigarette mainly includes a battery assembly and an atomizing assembly, the structure of which is shown in FIG. 1. The battery assembly includes an end cap 11, a microphone controller 12, a microphone seat 13, a battery 14, a battery sleeve 15, a lower electrode 16, an electrode fixing seat 17 and a connecting seat 18. The atomizing assembly includes a connector 20, an upper electrode 21, an upper insulating ring 22, an atomizing seat 23, an atomizing device 24, a PVC fiberglass sleeving 25, a liquid storage cotton 26, an atomizing sleeve 27 and a mouthpiece cover 28.

In conjunction with FIG. 1, the electronic cigarette can work normally by connecting the connecting seat 18 in the battery assembly to the connector 20 in the atomizing assembly. The inventor found that, the existing electronic cigarettes may be used in combination as long as connectors of the battery assembly and the atomizing assembly can be connected, irrespective of brands of the electronic cigarettes. Thus, when the battery assembly and the atomizing assembly, which are not matched, are used in combination, the power of the heating wire in the atomizing device does not match the power of the battery, which may cause damages to the electronic cigarette, for example battery overheat or battery leakage, and may further shorten the service life of the electronic cigarettes. Since the existing battery assembly and atomizing assembly can be used in any combination, it is apt to cause the mixed use of cigarette liquids having different flavors and the mixed use of the battery assembly and the atomizing assembly from different manufacturers, which may cause a poor user experience, hinders a user from knowing about the manufacturers and the brands, and is not beneficial for the user to quit smoking.

SUMMARY

In view of this, a battery assembly and an atomizing assembly of an electronic cigarette, and an electronic cigarette are provided according to the present application, which may effectively solve the problem in the conventional technology that damages on the electronic cigarette, for example battery overheat or battery leakage, may be caused in a case that the battery assembly and the atomizing assembly, which are not matched, are used in combination.

To achieve the above object, the present application provides the following technical solutions.

A battery assembly of an electronic cigarette is configured to form an electronic cigarette in combination with an atomizing assembly, wherein the atomizing assembly is provided with a substance to be detected, and the battery assembly includes:

a spectrum identification device, arranged on the battery assembly and configured to obtain spectrum information of the substance to be detected; and a microcontroller, connected with the spectrum identification device and configured to control a circuit between the battery assembly and the atomizing assembly to be switched on in a case that the microcontroller determines that the spectrum information of the substance to be detected matches a preset information, to enable the electronic cigarette to work normally.

Preferably, the spectrum identification device includes a light emitting module and a light receiving and converting module;

the light emitting module is connected with the microcontroller and configured to generate light with a preset wavelength to irradiate the substance to be detected; and the light receiving and converting module is configured to receive second light formed by irradiating the substance to be detected with the light having the preset wavelength, and convert the second light to an electrical signal and output the electrical signal to the microprocessor, and the second light includes diffracted light and transmitted light.

Preferably, the light emitting module is an infrared light emitting module, and the infrared light emitting module includes:

an infrared light source, configured to emit infrared light;

a parabolic reflector, configured to reflect the infrared light to obtain reflected light;

a digital frequency synthesizer, connected with the microprocessor and configured to perform frequency processing on a control signal sent from the microprocessor to generate a first signal;

a radio frequency driver, connected with the digital frequency synthesizer and configured to perform low pass filtering and power amplification on the first signal to generate a second signal; and an acousto-optic tunable filter, connected with the radio frequency driver and configured to process the reflected light according to the second control signal to generate the light with the preset wavelength and transmit the light with the preset wavelength to the substance to be detected.

Preferably, the infrared light emitting module further includes:

a modulator, arranged between the parabolic reflector and the acousto-optic tunable filter and configured to suppress noise.

Preferably, the light receiving and converting module includes:

an infrared detector group, configured to detect the second light and convert the second light into an electrical signal, wherein the infrared detector group includes a first infrared detector and a second infrared detector;

an adjustment circuit, connected with the infrared detector group and configured to amplify the electrical signal, wherein the adjustment circuit includes a first preamplifier, a second preamplifier, a two-stage amplifier and a shaping circuit;

a detection circuit, connected with the adjustment circuit and configured to detect an output signal of the adjustment circuit;

a low pass filter circuit, connected with the detection circuit and configured to perform filtering on an output signal of the detection circuit; and an analog to digital conversion circuit, connected with the low pass filter circuit and configured to perform analog to digital conversion on an output signal of the low pass filter circuit.

Preferably, the radio frequency driver includes:

a low pass filter circuit, connected with the digital frequency synthesizer;

an amplification circuit, connected with the low pass filter circuit and configured to amplify an output signal of the low pass filter circuit; and a power amplification circuit, connected with the amplification circuit and configured to perform power amplification on an output signal of the amplification circuit.

Preferably, the light receiving and converting module further includes:

a converging lens, configured to converge the second light to the infrared detector.

Preferably, the battery assembly further includes:

a notification device, electrically connected to the microprocessor and configured to show a matching result from the microprocessor, and the notification device is an alarm or an indicator light.

An atomizing assembly of an electronic cigarette is configured to form an electronic cigarette in combination with a battery assembly, wherein the atomizing assembly is provided with a substance to be detected, and a spectrum of the substance to be detected is to be matched by the battery assembly.

An electronic cigarette includes a battery assembly and an atomizing assembly, wherein the battery assembly is the battery assembly according to any one of the above technical solutions, and the atomizing assembly is the atomizing assembly according to any one of the above technical solutions.

According to the above technical solutions, compared to the conventional technology, the present application provides a battery assembly of an electronic cigarette which is configured to form an electronic cigarette in combination with an atomizing assembly. The atomizer of the electronic cigarette is provided with a substance to be detected, and the battery assembly is provided with a spectrum identification device and a microcontroller. The spectrum identification device is arranged on the battery assembly and is configured to obtain spectrum information of the substance to be detected. The microcontroller is connected with the spectrum identification device and configured to determine whether the spectrum information of the substance to be detected matches a preset information, and in a case that the spectrum information of the substance to be detected matches the preset information, the microcontroller controls a circuit between the battery assembly and the atomizing assembly to be switched on to enable the electronic cigarette to work normally. Thus, the electronic cigarette can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

BRIEF DESCRIPTION OF THE DRAWINGS

For more clearly illustrating embodiments of the present application or the technical solution in the conventional technology, drawings referred to describe the embodiments or the conventional technology will be briefly described hereinafter. Apparently, the drawings in the following description are only several embodiments of the present application, and for the person skilled in the art other drawings may be obtained based on these drawings without any creative efforts.

FIG. 5 is a schematic block diagram of another circuit of the electronic cigarette according to the present application;

FIG. 6 is a schematic block diagram of another circuit of the electronic cigarette according to the present application;

FIG. 7 is a schematic block diagram of another electronic cigarette according to the present application;

Figure 1:
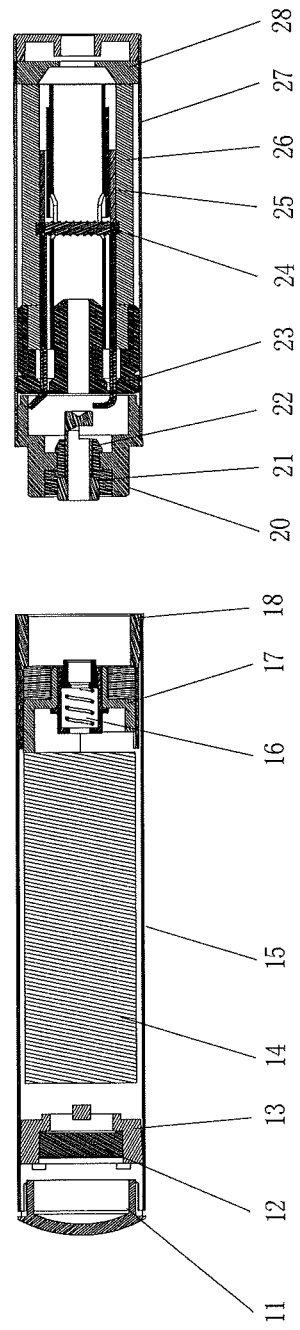
FIG. 1 is a schematic view showing the structure of an electronic cigarette in the conventional technology.

| Reference Numerals: | | |
|---|---|---|
| 11 end cap, | 12 microphone controller, | 13 microphone seat, |
| 14 battery, | 15 battery sleeve, | 16 lower electrode, |
| 17 electrode fixing seat, | 18 connecting seat, | 20 connector, |
| 21 upper electrode, | 22 upper insulating ring, | 23 atomizing seat, |
| 24 atomizing device, | 25 PVC fiberglass sleeving, | 26 liquid storage cotton, |
| 27 atomizing sleeve, | 28 mouthpiece cover, | 29 substance to be detected |

DETAILED DESCRIPTION

A battery assembly and an atomizing assembly of an electronic cigarette, and an electronic cigarette are provided according to the present application, wherein the electronic cigarette has an identification function to ensure that the electronic cigarette can be normally used only when the battery assembly and the atomizing assembly are matched, thereby avoiding damage to connectors of the electronic cigarette caused by mismatching, and avoiding unnecessary troubles caused by interchange between connectors of electronic cigarettes in different brands.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the protection scope of the present application.

First Embodiment

Figure 2:
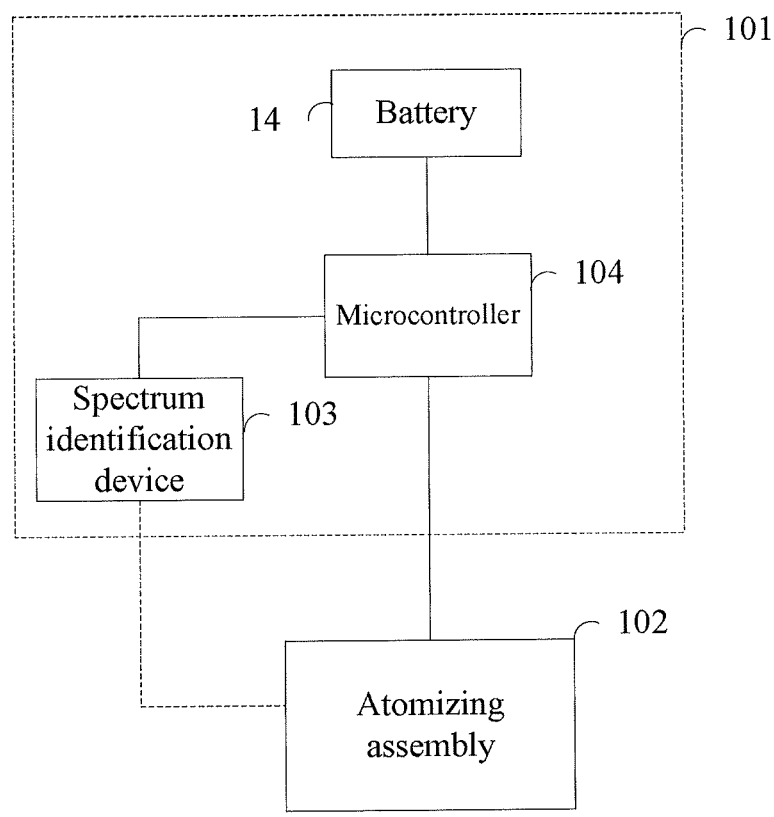
FIG. 2 is a schematic block diagram of an electronic cigarette according to an embodiment of the present application.

Referring to FIG. 2, a battery assembly 101 of an electronic cigarette according to an embodiment of the present application is configured to form an electronic cigarette in combination with an atomizing assembly 102. The atomizing assembly 102 is provided with a substance to be detected, and the battery assembly 101 includes a spectrum identification device 103 and a microcontroller 104.

The spectrum identification device is arranged on the battery assembly and configured to obtain spectrum information of the substance to be detected. The microcontroller is connected with the spectrum identification device and configured to determine whether the spectrum information of the substance to be detected matches a preset information, and in a case that the spectrum information of the substance to be detected matches the preset information, the microcontroller controls a circuit between the battery assembly and the atomizing assembly to be switched on to enable the electronic cigarette to work normally; and in a case that the spectrum information of the substance to be detected does not match the preset information, the microcontroller controls the circuit between the battery assembly and the atomizing assembly to be switched off to power off the electronic cigarette, that is, the electronic cigarette cannot work at this time.

Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

Figure 3:
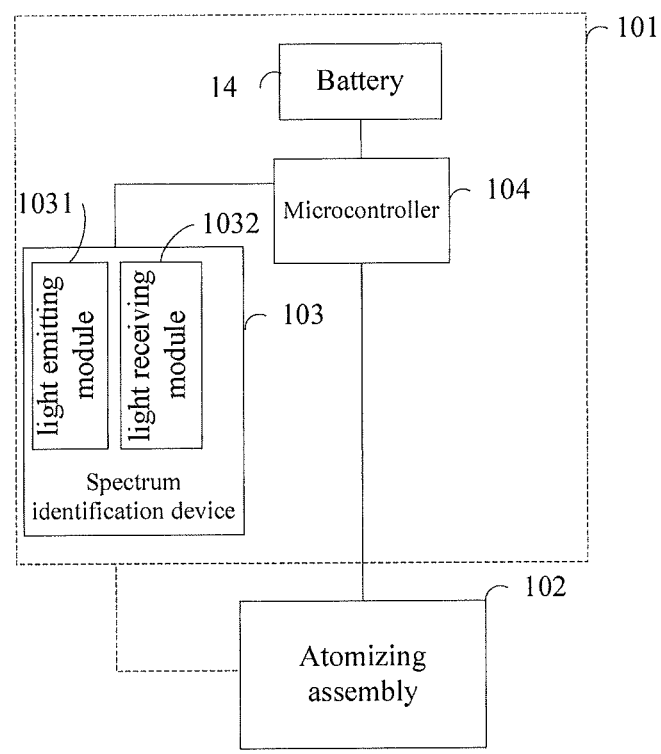
FIG. 3 is a schematic block diagram of an electronic cigarette according to the present application.

Preferably, as shown in FIG. 3, in this embodiment, the spectrum identification device may further include a light emitting module 1031 and a light receiving and converting module 1032. The light emitting module is connected with the microcontroller and configured to generate light with a preset wavelength to irradiate the substance to be detected. The light receiving and converting module is configured to receive second light formed by irradiating the substance to be detected with the light having the preset wavelength, and convert the second light to an electrical signal and output the electrical signal to the microprocessor. The second light may include diffracted light and transmitted light.

Figure 4:
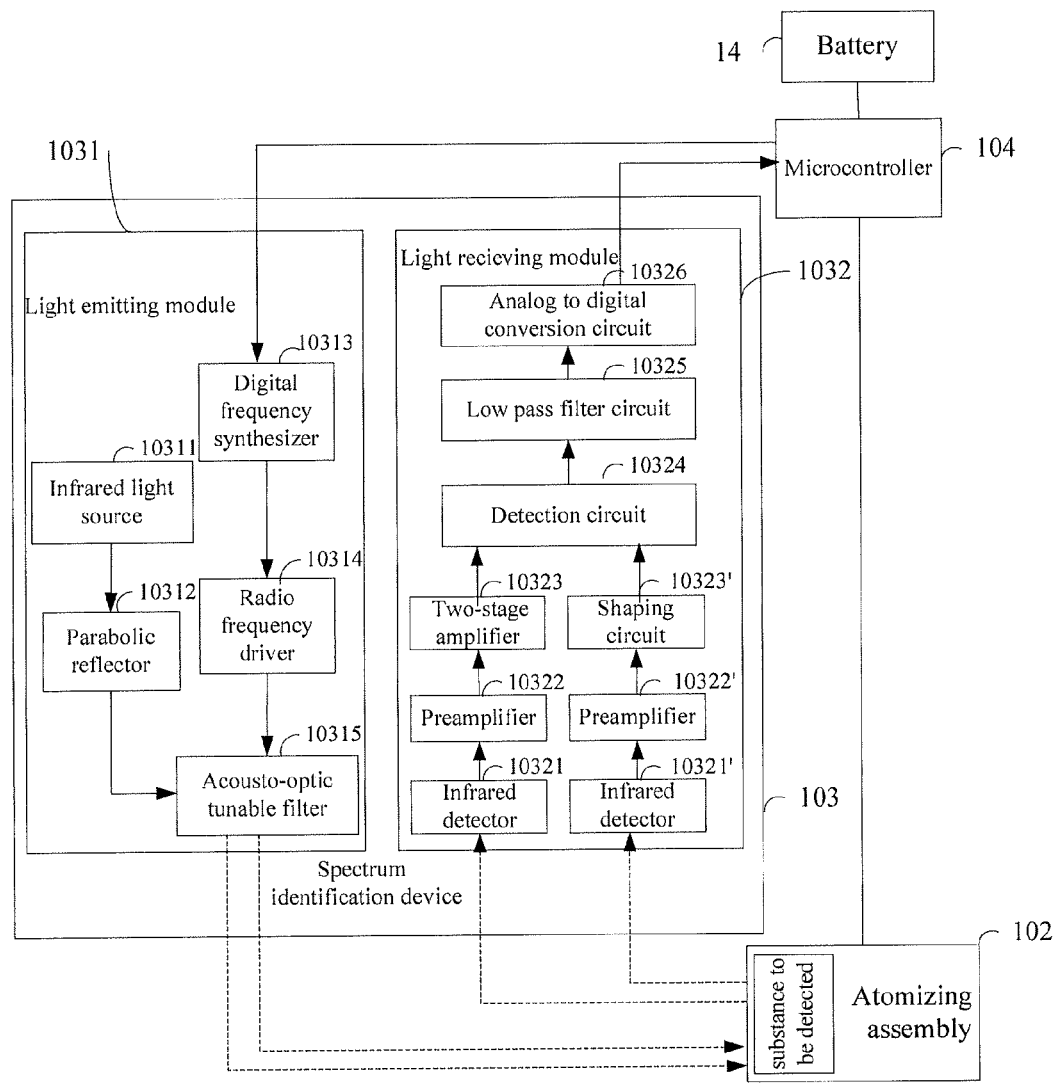
FIG. 4 is a schematic block diagram of a circuit of an electronic cigarette according to the present application.

This embodiment further provides a circuit structure of the light emitting module and the light receiving module. Referring to FIG. 4, the light emitting module is an infrared light emitting module, and the infrared light emitting module includes an infrared light source 10311, a parabolic reflector 10312, a digital frequency synthesizer 10313, a radio frequency driver 10314 and an acousto-optic tunable filter 10315.

The infrared light source 10311 emits infrared light. The parabolic reflector 10312 is configured to reflect the infrared light to obtain reflected light. The digital frequency synthesizer 10313 is connected with the microcontroller 104 and is configured to perform frequency processing on a control signal sent from the microcontroller 104 to generate a first signal. The radio frequency driver 10314 is connected with the digital frequency synthesizer 10313 and is configured to perform low pass filtering and power amplification on the first signal to generate a second signal. The acousto-optic tunable filter 10315 is connected with the radio frequency driver 10314 and is configured to process the reflected light according to the second control signal to generate the light with the preset wavelength and transmit the light with the preset wavelength to the substance to be detected.

It should be noted that, the radio frequency driver 10314 may include a low pass filter circuit, an amplification circuit and a power amplification circuit. The low pass filter circuit is connected with the digital frequency synthesizer 10313. The amplification circuit is connected with the low pass filter circuit and is configured to amplify an output signal of the low pass filter circuit. The power amplification circuit is connected with the amplification circuit and is configured to perform power amplification on an output signal of the amplification circuit.

Preferably, the light receiving and converting module includes an infrared detector group, an adjustment circuit, a detection circuit 10324, a low pass filter circuit 10325 and an analog to digital conversion circuit 10326.

The infrared detector group is configured to detect the second light and convert the second light into an electrical signal. It should be noted that, the infrared detector group includes a first infrared detector 10321 and a second infrared detector 10321'. The adjustment circuit is connected with the infrared detector group and is configured to amplify the electrical signal. Preferably, the adjustment circuit may further include a first preamplifier 10322, a second preamplifier 10322', a two-stage amplifier 10323 and a shaping circuit 10323'. The detection circuit 10324 is connected with the adjustment circuit and is configured to detect an output signal of the adjustment circuit, i.e., performing a cross-correlation function calculation to remove noise without the same frequency and the same phase. The low pass filter circuit 10325 is connected with the detection circuit 10324 and is configured to perform filtering on an output signal of the detection circuit 10324. The analog to digital conversion circuit 10326 is connected with the low pass filter circuit 10325 and is configured to perform analog to digital conversion on an output signal of the low pass filter circuit 10325.

The working principle of the spectrum identification device is briefly described hereinafter in conjunction with the above connection relationship. The detection is performed based on the fact that each substance has a specific spectrum absorption characteristic, i.e., different gases have different molecular or atomic structures, thus have different characteristic absorption wavelengths. Then an absorption peak of the substance at a specific wavelength and a wavelength value at the characteristic peak are determined based on the spectrum, and then whether the spectrum of the substance to be detected is the spectrum of the preset substance is determined. In a case that the controller determines that the detected spectrum does not match the preset spectrum, the controller controls the circuit between the battery assembly and the atomizing assembly to be switched off to power off the electronic cigarette, thereby efficiently avoids the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

Second Embodiment

Figure 5:
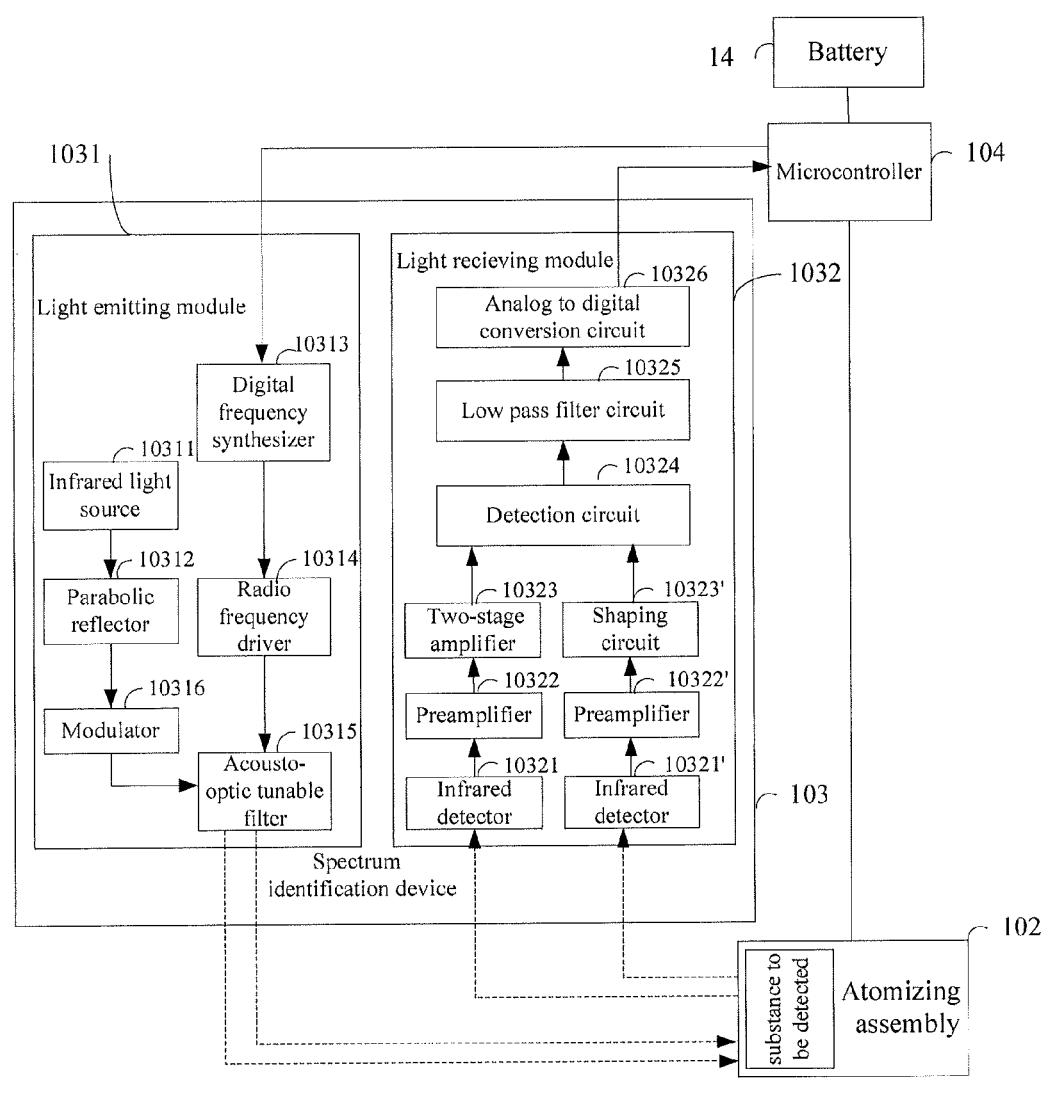

On the basis of the embodiment described above, this embodiment further provides a specific structure of an electronic cigarette. Compared with the first embodiment, in this embodiment shown in FIG. 5, the light emitting module 1031 of the spectrum identification device further includes a modulator 10316. The modulator 10316 is arranged between the parabolic reflector 10312 and the acousto-optic tunable filter 10315 and is configured to suppress noise. The working principle of other parts of the circuit in this embodiment is similar to that of the first embodiment, which will not be described herein.

Figure 6:
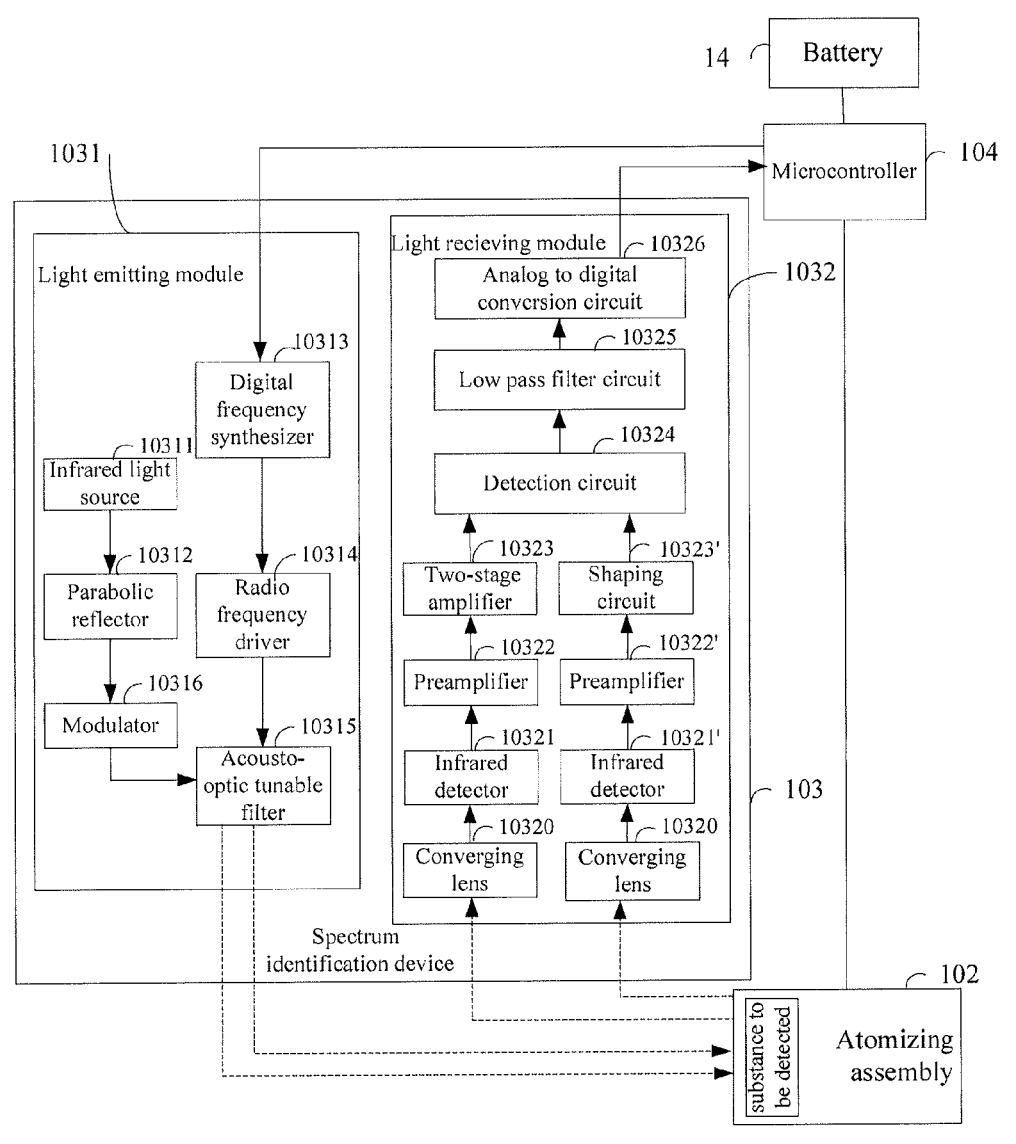

In addition, as shown in FIG. 6, on the basis of the first embodiment, in this embodiment, a converging lens 10320 may be arranged between the infrared detector 10321 of the light receiving module 1032 and the atomizing assembly 102, and a converging lens 10320' may be arranged between the infrared detector 10321' of the light receiving module 1032 and the atomizing assembly 102. In this way, the light passing through the substance to be detected may be converged better, thereby making the detection more accurate.

Third Embodiment

Figure 7:
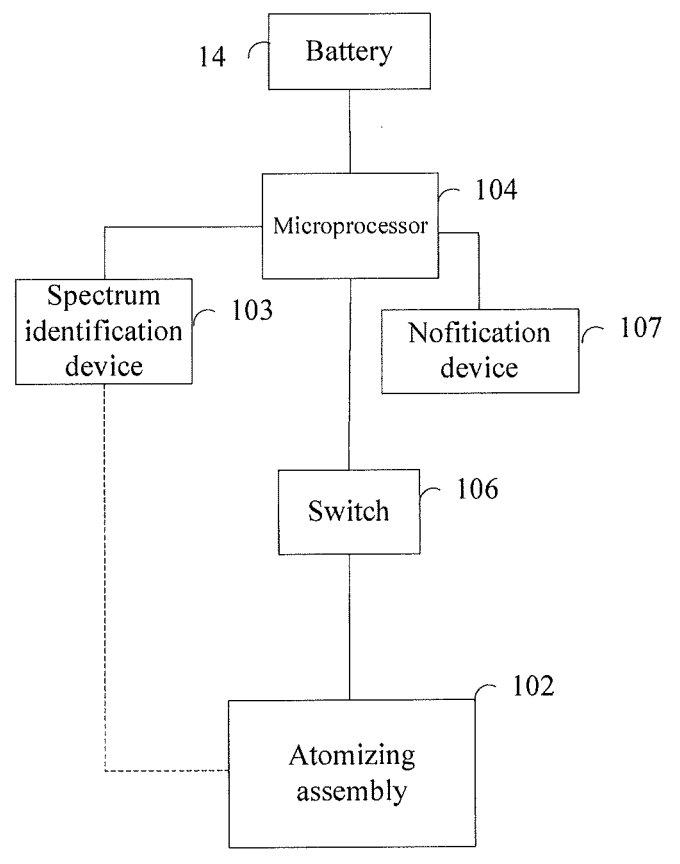

Referring to FIG. 7, a battery assembly of an electronic cigarette is provided according to this embodiment of the present application, and is adapted to form an electronic cigarette in combination with an atomizing assembly 102. The battery assembly includes a spectrum identification device 103, a microprocessor 104 and a switch 106.

The spectrum identification device 103 is configured to detect spectrum information of the substance to be detected on the atomizing assembly. The microcontroller 104 is connected with the spectrum identification device 103 and configured to determine whether the spectrum information of the substance to be detected matches a preset information, and in a case that the spectrum information of the substance to be detected matches the preset information, the microcontroller controls a circuit between the battery assembly and the atomizing assembly to be switched on, and at this time, the switch 106 is pressed, then the electronic cigarette may work normally; and in a case that the spectrum information of the substance to be detected does not match the preset information, the microprocessor controls the circuit between the battery assembly and the atomizing assembly to be switched off to power off the electronic cigarette, thus the electronic cigarette cannot work normally.

It should be noted that, the switch 106 may be a pneumatic sensor switch or a switch having mechanical button. Preferably, this embodiment also provides a device 107 for notifying identification result. The device is electrically connected to the microprocessor, and is configured to notify the identification result of the microprocessor. The device may be an alarm or an indicator light, and the alarm may be a buzzer alarm, a loudspeaker or the like.

Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

Fourth Embodiment

In addition to the embodiments described above, this embodiment further provides an atomizing assembly of an electronic cigarette, and a substance to be detected is arranged on an upper electrode of the atomizing assembly at a position close to a battery assembly. In this embodiment, the upper electrode is provided with an outer electrode and an inner electrode which are sleevedly engaged, and the substance to be detected is arranged on the inner electrode.

According to this embodiment, an electronic cigarette may be formed by combining the atomizing assembly with the battery assembly. Therefore, this embodiment further provides an electronic cigarette including the battery assembly and the atomizing assembly, and the battery assembly includes the microcontroller and the spectrum identification device described in any one of the above embodiments, and a substance to be detected is arranged on an upper electrode of the atomizing assembly at a position close to the battery assembly.

Figure 8:
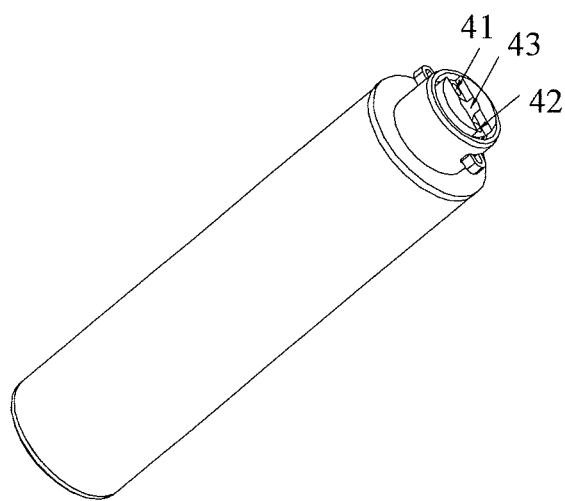
FIG. 8 is a perspective view of an atomizing assembly according to an embodiment of the present application.
Figure 9:
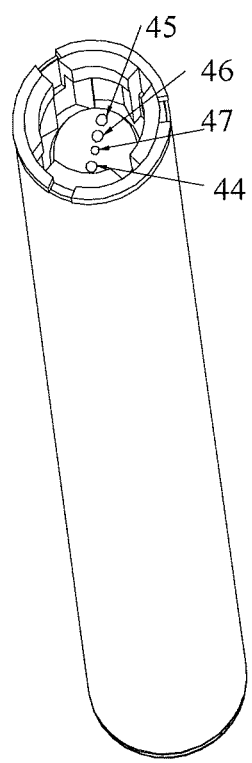
FIG. 9 is a schematic view showing the structure of a battery assembly according to an embodiment of the present application.

Reference is made to FIG. 8 and FIG. 9, which illustrates installing positions of the spectrum identification device and the microcontroller according to this embodiment. Of course, the positions of the spectrum identification device and the microcontroller are not limited to this, and the description herein is only exemplary.

Figure 10:
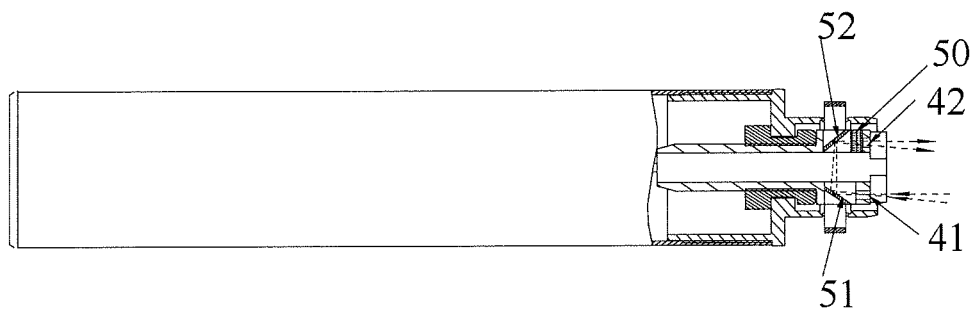
FIG. 10 is a schematic partial sectional view showing the structure of an atomizing assembly according to an embodiment of the present application.

In FIG. 10, a substance to be detected 50 is installed at a top portion of a connecting part of the atomizing assembly, and accordingly, a spectrum identification device 103 is provided at a top portion of the battery assembly. The spectrum identification device 103 is arranged inside the battery assembly and is not shown, and the specific position of the spectrum identification device 103 is not limited. As shown in FIG. 8, the inner electrode of the atomizing assembly is provided with a light inlet hole 41, a light outlet hole 42 and an air hole 43; and accordingly, as shown in FIG. 9, the battery assembly is provided with a light emitting hole 44 corresponding to the light inlet hole 41, and a transmitted light receiving hole 45 and a diffracted light receiving hole 46 which are configured to receive the light emitted from the light outlet hole 42 after passing through the substance to be detected, and the air hole 43 cooperates with an air hole 47 arranged on the battery assembly. In a case that it is determined that the spectrum information of the substance to be detected on the atomizing assembly read by the spectrum identification device matches the preset information, the electronic cigarette is enabled to work normally.

Referring to FIG. 8, the substance to be detected is arranged between the light inlet hole 41 and the light outlet hole 42, and the transmitting of light is achieved by two planar mirrors. As shown in FIG. 10, light entered through the light inlet hole 41 is reflected to the substance to be detected by a first planar mirror 51 and a second planar mirror 52, and the light passed through the substance to be detected 50 is emitted through the light outlet hole 42.

In summary, a battery assembly of an electronic cigarette according to the present application is adapted to form an electronic cigarette in combination with an atomizing assembly. The atomizer of the electronic cigarette is provided with a substance to be detected, and the battery assembly is provided with a spectrum identification device and a microcontroller. The spectrum identification device is arranged on the battery assembly and is configured to obtain spectrum information of the substance to be detected. The microcontroller is connected with the spectrum identification device and configured to determine whether the spectrum information of the substance to be detected matches a preset information, and in a case that the spectrum information of the substance to be detected matches the preset information, the microcontroller controls a circuit between the battery assembly and the atomizing assembly to be switched on to enable the electronic cigarette to work normally. Thus, the electronic cigarette can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

The above embodiments are described in a progressive manner. Each of the embodiments is mainly focused on describing its differences from other embodiments, and references may be made among these embodiments with respect to the same or similar portions among these embodiments. For the device in the embodiments, the description thereof is relatively simpler since it is corresponding to the method disclosed in the embodiments, hence, related parts of the device can refer to the description of the method.

Based on the above description of the disclosed embodiments, the person skilled in the art is capable of carrying out or using the present application. It is obvious for the person skilled in the art to make many modifications to these embodiments. The general principle defined herein may be applied to other embodiments without departing from the spirit or scope of the present application. Therefore, the present application is not limited to the embodiments illustrated herein, but should be defined by the broadest scope consistent with the principle and novel features disclosed herein.

The invention claimed is:

1. A battery assembly of an electronic cigarette, configured to form the electronic cigarette in combination with an atomizing assembly, wherein the atomizing assembly is provided with a substance to be detected, and the battery assembly comprises:
   a spectrum identification device, arranged on the battery assembly and configured to obtain spectrum information of the substance to be detected; and
   a microcontroller, electrically connected with the spectrum identification device and configured to control a circuit between the battery assembly and the atomizing assembly to be switched on in a case that the microcontroller determines that the spectrum information of the substance to be detected matches a preset information, to enable the electronic cigarette to work normally.

2. The battery assembly according to claim 1, wherein the spectrum identification device comprises a light emitting module and a light receiving and converting module;
   the light emitting module is electrically connected with the microcontroller and configured to generate light with a preset wavelength to irradiate the substance to be detected; and
   the light receiving and converting module is electrically connected with the microcontroller and configured to receive second light formed by irradiating the substance to be detected with the light having the preset wavelength, and convert the second light to an electrical signal and output the electrical signal to the microcontroller, and the second light comprises diffracted light and transmitted light.

3. The battery assembly according to claim 2, wherein the light emitting module is an infrared light emitting module, and the infrared light emitting module comprises:
   an infrared light source, configured to emit infrared light;
   a parabolic reflector, configured to reflect the infrared light to obtain reflected light;
   a digital frequency synthesizer, electrically connected with the microcontroller and configured to perform frequency processing on a control signal sent from the microcontroller to generate a first signal;
   a radio frequency driver, electrically connected with the digital frequency synthesizer and configured to perform low pass filtering and power amplification on the first signal to generate a second signal; and
   an acousto-optic tunable filter, electrically connected with the radio frequency driver and configured to process the reflected light according to the second control signal to generate the light with the preset wavelength and transmit the light with the preset wavelength to the substance to be detected.

4. The battery assembly according to claim 3, wherein the infrared light emitting module further comprises:
   a modulator, arranged between the parabolic reflector and the acousto-optic tunable filter and configured to suppress noise.

5. The battery assembly according to claim 2, wherein the light receiving and converting module comprises:
   an infrared detector group, configured to detect the second light and convert the second light into an electrical signal, wherein the infrared detector group comprises a first infrared detector and a second infrared detector;
   an adjustment circuit, electrically connected with the infrared detector group and configured to amplify the electrical signal, wherein the adjustment circuit comprises a first preamplifier, a second preamplifier, a two-stage amplifier and a shaping circuit;

a detection circuit, electrically connected with the adjustment circuit and configured to detect an output signal of the adjustment circuit;
a low pass filter circuit, electrically connected with the detection circuit and configured to perform filtering on an output signal of the detection circuit; and
an analog to digital conversion circuit, electrically connected with the low pass filter circuit and configured to perform analog to digital conversion on an output signal of the low pass filter circuit.

6. The battery assembly according to claim 3, wherein the radio frequency driver comprises:
a low pass filter circuit, electrically connected with the digital frequency synthesizer;
an amplification circuit, electrically connected with the low pass filter circuit and configured to amplify an output signal of the low pass filter circuit; and
a power amplification circuit, electrically connected with the amplification circuit and configured to perform power amplification on an output signal of the amplification circuit.

7. The battery assembly according to claim 5, wherein the light receiving and converting module further comprises:
a converging lens, configured to converge the second light to the infrared detector.

8. The battery assembly according to claim 1, wherein the battery assembly further comprises:
a notification device, electrically connected to the microcontroller and configured to show a matching result from the microcontroller, and the notification device is an alarm or an indicator light.

9. An electronic cigarette, comprising a battery assembly and an atomizing assembly, wherein the atomizing assembly is provided with a substance to be detected, and the battery assembly comprises:
a spectrum identification device, arranged on the battery assembly and configured to obtain spectrum information of the substance to be detected; and
a microcontroller, electrically connected with the spectrum identification device and configured to control a circuit between the battery assembly and the atomizing assembly to be switched on in a case that the microcontroller determines that the spectrum information of the substance to be detected matches a preset information, to enable the electronic cigarette to work normally the battery assembly is the battery assembly according to any one of claims 1 to 8.

10. The electronic cigarette according to claim 9, wherein the spectrum identification device comprises a light emitting module and a light receiving and converting module;
the light emitting module is electrically connected with the microcontroller and configured to generate light with a preset wavelength to irradiate the substance to be detected; and
the light receiving and converting module is electrically connected with the microcontroller and configured to receive second light formed by irradiating the substance to be detected with the light having the preset wavelength, and convert the second light to an electrical signal and output the electrical signal to the microcontroller, and the second light comprises diffracted light and transmitted light.

11. The electronic cigarette according to claim 10, wherein the light emitting module is an infrared light emitting module, and the infrared light emitting module comprises:
an infrared light source, configured to emit infrared light;
a parabolic reflector, configured to reflect the infrared light to obtain reflected light;
a digital frequency synthesizer, electrically connected with the microcontroller and configured to perform frequency processing on a control signal sent from the microcontroller to generate a first signal;
a radio frequency driver, electrically connected with the digital frequency synthesizer and configured to perform low pass filtering and power amplification on the first signal to generate a second signal; and
an acousto-optic tunable filter, electrically connected with the radio frequency driver and configured to process the reflected light according to the second control signal to generate the light with the preset wavelength and transmit the light with the preset wavelength to the substance to be detected.

12. The electronic cigarette according to claim 11, wherein the infrared light emitting module further comprises:
a modulator, arranged between the parabolic reflector and the acousto-optic tunable filter and configured to suppress noise.

13. The electronic cigarette according to claim 10, wherein the light receiving and converting module comprises:
an infrared detector group, configured to detect the second light and convert the second light into an electrical signal, wherein the infrared detector group comprises a first infrared detector and a second infrared detector;
an adjustment circuit, electrically connected with the infrared detector group and configured to amplify the electrical signal, wherein the adjustment circuit comprises a first preamplifier, a second preamplifier, a two-stage amplifier and a shaping circuit;
a detection circuit, electrically connected with the adjustment circuit and configured to detect an output signal of the adjustment circuit;
a low pass filter circuit, electrically connected with the detection circuit and configured to perform filtering on an output signal of the detection circuit; and
an analog to digital conversion circuit, electrically connected with the low pass filter circuit and configured to perform analog to digital conversion on an output signal of the low pass filter circuit.

14. The electronic cigarette according to claim 11, wherein the radio frequency driver comprises:
a low pass filter circuit, electrically connected with the digital frequency synthesizer;
an amplification circuit, electrically connected with the low pass filter circuit and configured to amplify an output signal of the low pass filter circuit; and
a power amplification circuit, electrically connected with the amplification circuit and configured to perform power amplification on an output signal of the amplification circuit.

15. The electronic cigarette according to claim 13, wherein the light receiving and converting module further comprises:
a converging lens, configured to converge the second light to the infrared detector.

16. The electronic cigarette according to claim 9, wherein the battery assembly further comprises:
a notification device, electrically connected to the microcontroller and configured to show a matching result from the microcontroller, and the notification device is an alarm or an indicator light.

17. A method for determining compatibility of a battery assembly with an atomizing assembly, the battery assembly and the atomizing assembly being configured to form an electronic cigarette, the atomizing assembly being provided with a substance to be detected; wherein the method comprises:
- obtaining spectrum information of the substance to be detected by a spectrum identification device arranged on the battery assembly;
- determining, by a microcontroller electrically connected with the spectrum identification device, whether the spectrum information of the substance to be detected matches a preset information; and
- controlling, by the microcontroller, a circuit between the battery assembly and the atomizing assembly to be switched on in a case that the microcontroller determines that the spectrum information of the substance to be detected matches the preset information, to enable the electronic cigarette to work normally.

18. The method according to claim 17, wherein the spectrum identification device comprises a light emitting module and a light receiving and converting module both electrically connected with the microcontroller, and
- the obtaining spectrum information of the substance to be detected by the spectrum identification device arranged on the battery assembly comprises:
  - generating light with a preset wavelength by the light emitting module to irradiate the substance to be detected, to form second light, wherein the second light comprises diffracted light and transmitted light;
  - receiving the second light by the light receiving and converting module;
  - converting the second light to an electrical signal by the light receiving and converting module; and
  - outputting the electrical signal to the microcontroller by the light receiving and converting module.

19. The method according to claim 18, wherein the generating light with a preset wavelength by the light emitting module to irradiate the substance to be detected, to form second light comprises:
- emitting infrared light by an infrared light source;
- reflecting the infrared light to obtain reflected light by a parabolic reflector;
- performing, by a digital frequency synthesizer electrically connected with the microcontroller, frequency processing on a control signal sent from the microcontroller to generate a first signal;
- performing, by a radio frequency driver electrically connected with the digital frequency synthesizer, low pass filtering and power amplification on the first signal to generate a second signal;
- processing, by an acousto-optic tunable filter electrically connected with the radio frequency driver, the reflected light according to the second control signal to generate the light with the preset wavelength; and
- transmitting, by the acousto-optic tunable filter, the light with the preset wavelength to the substance to be detected.

20. The method according to claim 18, wherein after converting the second light to the electrical signal by the light receiving and converting module, the method further comprises:
- amplifying the electrical signal by an adjustment circuit electrically connected with the infrared detector group, wherein the adjustment circuit comprises a first preamplifier, a second preamplifier, a two-stage amplifier and a shaping circuit;
- detecting an output signal of the adjustment circuit by a detection circuit electrically connected with the adjustment circuit;
- performing filtering on an output signal of the detection circuit by a low pass filter circuit electrically connected with the detection circuit; and
- performing analog to digital conversion on an output signal of the low pass filter circuit by an analog to digital conversion circuit electrically connected with the low pass filter circuit.

* * * * *